United States Patent [19]

Hunter

[11] Patent Number: 5,254,709
[45] Date of Patent: Oct. 19, 1993

[54] METHOD FOR PREPARING STEARICALLY HINDERED ARYL PHOSPHITES

[75] Inventor: Bryon A. Hunter, Alpine, Utah

[73] Assignee: Uniroyal Chemical Company, Inc., Middlebury, Conn.

[21] Appl. No.: 935,663

[22] Filed: Aug. 24, 1992

Related U.S. Application Data

[63] Continuation of Ser. No. 447,988, Dec. 8, 1989, abandoned.

[51] Int. Cl.$^5$ .............................................. C07F 9/145
[52] U.S. Cl. ........................................ 558/96; 558/95; 558/194; 558/218
[58] Field of Search ................ 558/92, 194, 218, 95, 558/96

[56] References Cited

U.S. PATENT DOCUMENTS

| | | | |
|---|---|---|---|
| 2,733,226 | 1/1956 | Hunter | 549/512 |
| 3,467,735 | 9/1969 | Hunter | 558/194 |
| 3,533,989 | 10/1970 | Wescott, Jr. | 558/96 |
| 3,907,939 | 9/1975 | Robin et al. | 558/95 |
| 3,949,024 | 4/1976 | Beck et al. | 558/95 |
| 4,312,818 | 1/1982 | Maul et al. | 558/96 |
| 4,321,218 | 3/1982 | Rasberger et al. | 558/218 |
| 4,360,617 | 11/1982 | Muller et al. | 524/101 |
| 4,440,696 | 4/1984 | Maul et al. | 558/96 |

OTHER PUBLICATIONS

*Vulcanization of Elastomers* (Alliger and Sjothun, Editors) pp. 158–170 (1964).
Torii et al. Chemical Abstracts, vol. 94, No. 65055 (1981).
Brownbridge et al. Chemical Abstracts, vol. 110, No. 114951 (1989).

*Primary Examiner*—Emily Bernhardt
*Attorney, Agent, or Firm*—Raymond D. Thompson

[57] ABSTRACT

A new process is disclosed for the manufacture of hindered aryl phosphites using derivatives of mercaptothiazole or dithiocarbamic acid as catalysts. Ortho-tertiary alkyl aryl phosphites are produced by the reaction of a phosphorus trihalide with an ortho-tertiary alkyl phenolic compound in the presence of the aforementioned catalysts.

20 Claims, No Drawings

METHOD FOR PREPARING STEARICALLY HINDERED ARYL PHOSPHITES

This is a continuation of application Ser. No. 07/447,988 filed Dec. 8, 1989, now abandoned.

BACKGROUND OF THE INVENTION

The invention relates to a new process for the manufacture of hindered aryl phosphites using derivatives of mercapto thiazole or dithiocarbamic acid derivatives as catalysts. More particularly, ortho-tertiary alkyl aryl phosphites are produced by the reaction of a phosphorus tri halide with an ortho-tertiary alkyl phenolic compound in the presence of the aforementioned catalysts.

BACKGROUND ART

Aryl phosphite compounds are of great value as non discoloring stabilizers of polymers. Tris (p-nonyl phenyl) phosphite, as described in U.S. Pat. No. 2,733,226 is widely used as a stabilizer for rubbers and plastics. This compound is manufactured by reacting p-nonyl phenol with phosphorus trichloride. The reaction proceeds very well at moderate temperature and high yields of the liquid phosphite are readily obtained at relatively low cost. Special treatment of the product with certain acid sequestering agents improves the hydrolysis stability of the substance and the commercial material has been considered very satisfactory for many uses. More recently certain sterically hindered aryl phosphites have been developed which exhibit even greater resistance to hydrolysis and are preferred in certain applications where extreme resistance to water and steam is important. Of particular interest are a number of solid aryl phosphite compounds which contain tertiary alkyl groups ortho to the phosphite linkage.

The preparation of ortho tertiary alkyl aryl phosphites is more difficult than is the preparation of phosphites containing less hindering substituents. In fact it has proven impossible to obtain acceptable yields of good quality hindered aryl phosphites in the absence of catalysts.

The formation of ortho tertiary alkyl aryl phosphites is represented:

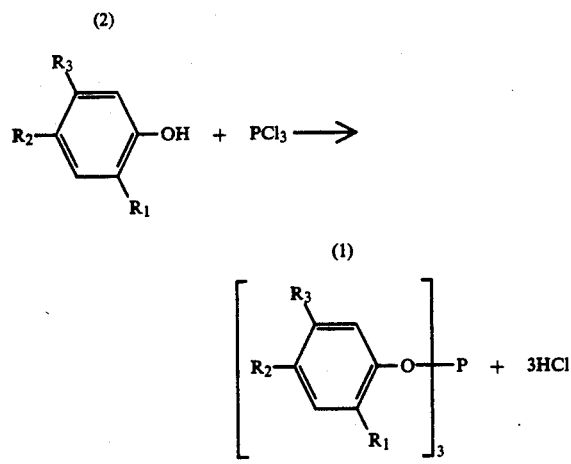

The highly hindering effect of the ortho tertiary alkyl group ($R_1$) greatly inhibits the reaction and in the absence of an effective catalyst the reaction remains incomplete even after extended periods of heating and substantial quantities of partially reacted intermediates remain in the product. Such partially unreacted intermediates are very undesirable (particularly in relation to hydrolysis stability) and such preparations are worthless in the intended application.

Early work showed that certain basic materials such as triethylamine, used in stoichiometric quantities as a hydrogen chloride scavenger (U.S. Pat. No. 3,533,989) gave yields as high as 80% of theory of the desired product. Other basic substances such as sodium ethylate, sodium amide and lithium butyrate are proposed as catalysts in the preparation of tris(2,4-di tertiary octyl phenyl) phosphite, preferably in the absence of solvents (U.S. Pat. No. 4,321,218). It is noteworthy, however, that the cited inventor prefers to use a stoichiometric quantity of tri ethyl amine in the preparation of the cited phosphite compound.

U.S. Pat. Nos. 4,312,818 and 4,440,696 disclose a wide variety of catalysts for the preparation of triaryl phosphites. These comprise amines, ammonium salts, amides of carboxylic acids and thiocarboxylic acids and also oxygen acids of phosphorus, non-aromatic nitrogen containing heterocycles and salts thereof, sulfones, sulfoxides and sulfonium salts, primary, secondary and tertiary phosphines and salts thereof, phosphine oxides, phosphine sulfides or esters of phosphoric acid.

The objects of the present invention are to provide catalysts for the preparation of sterically hindered triaryl phosphites which produce high yields of high quality products and which are free of disadvantages and complications associated with catalysts heretofore disclosed. The achievement of these objectives will be made apparent in the description that follows:

DETAILED DESCRIPTION OF THE INVENTION

The catalysts to be used according to the invention comprise several classes of organic compounds not previously described as catalysts for the production of phosphites.

They share the attribute that a central carbon atom is bonded to a sulfur atom and to two other hetro atoms. The following is a structural representation of the active portion of the catalyst molecules.

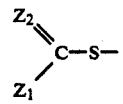

$Z_1$ is O, S or N.
$Z_2$ is N or S

Of course $Z_1$ and $Z_2$ may be further bonded to other substituents depending upon the valence as will be illustrated in Structures I-VII below which provide illustrative examples.

The first group of the new catalysts are properly described as mercapto thiazole derivatives. These compounds include the molecular arrangement of carbon, nitrogen and sulfur atoms outlined in (I).

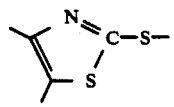

The free bonds on nitrogen and the two sulfur atoms may be attached to other atoms or groups as will be made clear in the list of compounds claimed in this invention. For example, the following compounds are included:

2-Mercaptobenzothiazole; Zinc salt of 2-mercaptobenzothiazole; Bis(benzothiazyl) disulfide; N-Tertiary butyl benzothiazole-2-sulfenamide; N-cyclohexyl benzothiazole-2-sulfenamide; N,N-dicyclohexyl benzothiazole-2-sulfenamide; N-morpholyl benzothiazole-2-sulfenamide; and 2-mercapto thiazole.

A structural representation (A) describes some of the compounds.

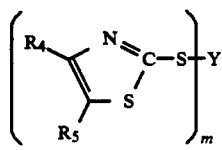

(A)

$R_4$ and $R_5$ individually are hydrogen, $C_1$–$C_{12}$ alkyl, $C_2$–$C_8$ branched or linear alkylene; $R_4$ and $R_5$ combinedly may be benzo, substituted phenyl, $C_2$–$C_{18}$ branched or linear alkylene; when m is 1, Y is hydrogen, alkylamino, cycloalkylamino, a monovalent metal, morpholino, $C_1$–$C_8$ alkyl, phenyl, substituted phenyl, or benzyl; and when m is 2, Y is a bond, divalent metal, $C_2$–$C_8$ alkylene, or alkylene diamine.

Preferred compounds are those in which $R_4$ and $R_5$ along with the adjacent carbons of the thiazole ring combinedly are benzo, and m is 1 or 2. Y is a bond or zinc, when m is 2. Y is hydrogen, alkylamino, cyclohexyl amino, dicyclohexyl amino, morpholino, zinc, when m=1.

More preferred are those in which R and R with the adjacent carbons combinedly are benzo, m is 1, Y is hydrogen or cyclohexylamino.

The second group of catalysts covered by the invention may be generally classified as derivatives of dithiocarbamic acid possessing the molecular arrangement of carbon, nitrogen and sulfur atoms outlined in structure (II).

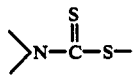

(II)

Here again the free bonds attached to nitrogen and sulfur are joined to other atoms or groups as clarified in the following list of compounds:
Tetra methyl thiuram disulfide
Tetra ethyl thiurim disulfide
Tetra propyl thiuram disulfide
Tetra butyl thiuram disulfide
Tetra benzyl thiuram disulfide
Tetra methyl thiuram monosulfide
Tetra ethyl thiuram monosulfide
Tetra propyl thiuram monosulfide
Tetra butyl thiuram monosulfide
Tetra benzyl thiuram monosulfide Structural representation B describes others of the foregoing compounds.

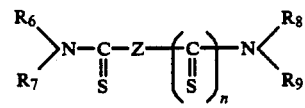

(B)

Z is —S—, —S—S—, S—metal—S; n=0, 1.

When n is 1 then $R_6$, $R_7$, $R_8$, $R_9$ are independently selected from hydrogen, $C_1$–$C_8$ branched or linear alkyl, benzo, phenyl, and substituted phenyl.

When n is 0, then $R_6$, $R_7$, $R_8$, $R_9$ are independently selected from $C_1$–$C_8$ alkyl, alkylene, or alkoxy and wherein $R_6$ and $R_7$ combined may be oxydialkylene. Most preferably $R_6$-$R_7$ and/or $R_8$-$R_9$ with the adjacent nitrogen forms a morpholino group.

The structures (III),(IV),(V) represent various mercaptothiazolines, mercaptobenzimidazoles and mercaptobenzoxadoles respectively:
a mercaptothiazoline derivative of structure (III);

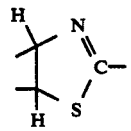

a mercaptobenzimidazole containing the structure (IV); and

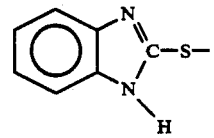

a mercaptobenzoxazole containing structure (V)

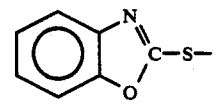

Various Thiocarbamyl sulfenamides and N-oxydiethylene Thiocarbamyl -N-oxydiethylenesulfenamide may also be used as catalysts.

It will be apparent to rubber chemists that many of the compounds listed are well known as vulcanization accelerators and for the most part are readily available at moderate cost. Such is not the case with many compounds previously proposed as catalysts for the preparation of aryl phosphites.

Unique and outstanding characteristics of the catalysts of the invention become apparent as these are applied in the preparation of hindered alkyl aryl phosphites. The hindered alkyl aryl phosphites of this invention are preferably of the triaryl phosphites of the formula (1).

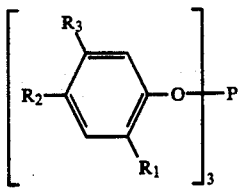

(1)

Preferred structures for $R_1$, $R_2$ and $R_3$ are t-butyl; t-amyl; t-octyl; t-nonyl; t-dodecyl; dimethyl benzyl;

The $PCl_3$ may incrementally be added to reactants. R1 must contain a tertiary carbon atom substituted ortho to the oxygen on the phenyl ring. The preferred substitutes are the tertiary alkyls, most preferably $C_4$–$C_{18}$ alkyls. However, it is believed that the tertiary carbon may be substituted with one or more branched alkyl, cycloalkyl or aryl groups, although the hindrance of such bulky groups may limit their commercial availability and reaction rates. Most preferred $R_1$ groups would be tertiary butyl, tertiary octyl, and tertiary amyl.

$R_2$ and $R_3$ are independently are selected from hydrogen, hydroxy, $C_4$–$C_{18}$ tertiary alkyl, $C_1$–$C_{20}$ alkyl; cycloalkyl, aryl, aralkyl, alkoxy. Preferred are hydrogen, tertiary alkyl, and hydroxy.

The phosphites of structure (1) are formed by the reaction of a phosphorus trihalide with hydroxy-substituted aromatic compound of the formula (2) in the presence or absence of a solvent.

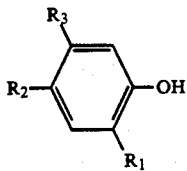

(2)

In another embodiment of the invention two different hydroxy-substituted aromatic compounds (i.e. two alkyl phenols) of the structural formula (2) types are sequentially reacted with the phosphorus trihalide with the first one being present in less than stoichemetric amounts (less than 3 mols per mol of phosporous trihalide). The second reaction completes the trihalide substitution. Thus, a (first alkyl phenol)2 - (second phenol)1 phosphite is formed.

The hydroxy-substituted aromatic compound is preferably 2-t-butylphenol, 2,4-di-butyl- phenol, 2,6-di-t-butylphenol, 2-(1,1-dimethylpropyl) phenol, 2-t-amylphenol, 2,4-di-t-amylphenol,2-t-octyl- phenol, di-t-octylphenol, t-nonylphenol, t-dodecyl- phenol, 2-(dimethylbenzyl)phenol, 2,5-di-tert-butyl hydroquinone 2,5-di-tert-amylhydroquinone.

The Reaction

For example, it has been clearly demonstrated that the preferred compounds of the invention are nicely compatible with the preparative reaction mixtures consisting of an ortho tertiary alkyl phenol, a suitable solvent and phosphorus trichloride. When warmed to reaction temperature the ingredients dissolve completely to form a clear solution and remain in solution until the crystalline product (the alkyl aryl phosphite) is produced at the later stages of the reaction. Indeed, with a sufficient amount of a suitable solvent all will remain in clear solution as hydrogen chloride is eliminated. Upon cooling the completed reaction mixture deposits the desired crystalline reaction product. The crystalline product can be filtered off and the resulting filtrate will retain the catalyst in a reusable condition. One can recharge the catalyst containing filtrate (along with any solvent washings) into the reactor and by adding new charges of alkyl phenol and phosphorus trichloride repeat the preparation with no additional catalyst. This can be repeated numerous times. An additional advantage of the instant invention's soluble catalysts is that they do not separate along with the phosphite product as an unwanted contaminant. In the case of the prior art triethylamine used as a catalyst, the amine will react with the evolving hydrogen chloride and will form the solvent insoluble amine hydrochloride which will contaminate the crystalline phosphite product and must be subsequently eliminated. Further, the triethylamine will be removed from the solvent and new amine must be added for a subsequent preparation.

The mode of reaction and the work up of solid tertiary alkyl aryl phosphite preparations employing the instant invention's preferred catalysts can be varied to suit the employment of equipment modifications. We have already described a process in which a proper mixture of ortho alkyl phenol, solvent, phosphorus trichloride and catalyst are heated for times sufficient for elimination of all hydrogen chloride and production of hot solvent solution of the product. Simple cooling of the mixture (preferably under agitation) produces the solid crystalline product which may be filtered off, washed with a proper solvent and dried. The filtrate, as mentioned before, retains the solvent and may be reused for a subsequent preparation.

A modification of the above described procedure involves the use of a sufficient amount of a suitable solvent to hold the product in solution even after cooling to ambient temperatures. The solution can then be transported to a different area where the solvent can be removed (usually under diminished pressure) to leave a crude solid product (still containing the catalyst and any unreacted alkyl phenol). Treatment of the crude product with a suitable solvent (reethanol, ethanol, isopropanol or a suitable hydrocarbon solvent) produces an insoluble purified product. Filtration will be a necessary step in this method as well as in the procedure previously described.

Any of a number of solvents can be used in the preparation of hindered aryl phosphites. Hexane, heptane, octane, nonane, decane, etc. can be used a well as benzene, toluene, xylenes naphtha etc. Other solvents may also be used, such as halogenated aliphatics. Certain are sometimes advantageously used in the work up of the products. Methanol, ethanol, isopropanol can wash out any unreacted intermediates along with residual catalysts. Under certain conditions the hindered aryl phosphites can be produced in the absence of solvents. In such cases the application of alcohols to the raw product can improve the purity of the phosphite.

The molar percent of catalyst per mole of the alkyl phenol of formula (2) should fall between about 0.005 to 10 mol %. The more preferred range is 0.01 to 2 mol percent. The most preferred range is 0.1 to 1 mol percent per mol of alkyl phenol.

The molar ratios of hydroxy substituted aromatic compound of formula (2) to phosphorus trihalide is between 2.5:1 and 4.5:1. Preferred would be 10% above or below the stoichemetric ratio of 3:1.

The amounts of solvent (if any) can vary widely and generally will range from 0.1 to 3 times the weight of reactants. The least amount useful will be that amount required to maintain the reaction mass in a liquid state at the reactor temperature.

The reaction temperatures are conveniently run at reflux temperature of the reaction mass, but other fixed and variable temperature profiles over the reaction period can be utilized to optimize yield, selectivity, etc.

The phosporous trihalide may, of course, be added incrementally to the reactor mass over a period of time to assure good control of reaction rate.

The modes of applying the new catalysts in the preparation of sterically hindered aryl phosphite compounds are illustrated in the following examples:

SYNTHESIS 1-9

Example 1

Preparation of tris(2,4-di-tertiary butyl phenyl)phosphite

In a 500 ml 3-necked flask equipped with thermometer, reflux condenser, and heating mantle was introduced 61.9 g (0.3 mole) of 2,4-di-tertiary butyl phenol, 0.3 g 2-mercaptobenzothiazole and 100 cc of hexane. To this mix (at room temperature) was then added 13.7 g (0.1 mole) of phosphorus trichloride. The mixture was gradually heated to reflux temperature over the course of one hour. Hydrogen chloride gas was rapidly evolved. The heating was continued for a total period of eight hours when the evolution of hydrogen chloride practically ceased. Nitrogen gas was passed through the clear solution to rid the mix of any residual hydrogen chloride. The hexane was then distilled off (diminished pressure) leaving a solid residue in the reaction flask. To this product was then added 100 cc of isopropanol. The stirred mixture formed a white suspension of crystalline powder. The product was filtered off, washed with a small amount of isopropanol and dried. Yield=61.2 g (94% of theory). The material melted at 181°-182° C.

Example 2

In a 500 ml 3-necked flask equipped with thermometer, reflux condenser, and heating mantle was introduced 103 g (½mole) 2,4-ditertiary butyl phenol, 0.3 g 2-mercaptobenzothiazole and 100 cc of heptane. 23.0 g (1/6 mole) of phosphorus trichloride was then added and the mixture was heated to reflux temperature for eight hours. Nitrogen was passed through the hot solution to sweep out any residual hydrogen chloride. A stirrer was attached and the mix was stirred and cooled (finally to 10° C.) whereupon tris(2,4-ditertiary butyl phenyl) phosphite separated as a white crystalline solid. This was filtered off and washed with 50 cc of heptane. The dried product weighed 91.28 g (85% of theory). The material melted at 178°-184° C.

Example 3

In a 500 ml 3-necked flask equipped with thermometer, reflux condenser, and heating mantle was introduced 103 g (½ mole) 2,4-ditertiary butyl phenol, 0.3 g bis (benzothiazyl) disulfide and 100 cc of hexane. 23.0 g (1/6 mole) of phosphorus trichloride was then added and the mixture was heated to reflux temperature for eight hours. Nitrogen was passed through the hot solution to sweep out any residual hydrogen chloride. A stirrer was attached and the mix was stirred and cooled (finally to 10° C.) whereupon tris(2,4-ditertiary butyl phenyl) phosphite separated as a white crystalline solid. This was filtered off and washed with 50 cc of heptane. The dried product weighed 83.87 g (78% of theory). The material melted at 181°-184° C.

Example 4

In a 500 ml 3-necked flask equipped with thermometer, reflux condenser, and heating mantle was introduced 103 g (½ mole) 2,4-ditertiary butyl phenol, 0.3 g of N-cyclohexyl benzothiazole-2-sulfenamide and 100 cc of hexane. 23.0 g (1/6 mole) of phosphorus trichloride was then added and the mixture was heated to reflux temperature for eight hours. Nitrogen was passed through the hot solution to sweep out any residual hydrogen chloride. A stirrer was attached and the mix was stirred and cooled (finally to 10° C.) whereupon tris(2,4-ditertiary butyl phenyl) phosphite separated as a white crystalline solid. This was filtered off and washed with 50 cc of heptane. The dried product weighed 96.68 g (90% of theory). The material melted at 178°-184° C.

Example 5

In a 500 ml 3-necked flask equipped with thermometer, reflux condenser, and heating mantle was introduced 103 g (½ mole) 2,4-ditertiary butyl phenol, 0.3 g of the zinc salt of 2-mercaptobenzothiazole and 100 cc of hexane. 23.0 g (1/6 mol) of phosphorus trichloride was then added and the mixture was heated to reflux temperature for eight hours. Nitrogen was passed through the hot solution to sweep out any residual hydrogen chloride. A stirrer was attached and the mix was stirred and cooled (finally to 10° C.) whereupon tris(2,4-ditertiary butyl phenyl) phosphite separated as a white crystalline solid. This was filtered off and washed with 50 cc of heptane. The dried product weighed 78.35 g (73% of theory). The material melted at 182°-186° C.

Example 6

In a 500 ml 3-necked flask equipped with thermometer, reflux condenser, and heating mantle was introduced 103 g (½ mole) 2,4-ditertiary butyl phenol, 0.3 g morpholyl-benzothiazole-2-sulfenamide and 100 cc of hexane. 23.0 g (1/6 mole) of phosphorus trichloride was then added and the mixture was heated to reflux temperature for eight hours. Nitrogen was passed through the hot solution to sweep out any residual hydrogen chloride. A stirrer was attached and the mix was stirred and cooled (finally to 10° C.) whereupon tris(2,4-ditertiary butyl phenyl) phosphite separated as a white crystalline solid. This was filtered off and washed with 50 cc of heptane. The dried product weighed 76.2 g (71% of theory). The material melted at 179°-180° C.

Example 7

In a 500 ml 3-necked flask equipped with thermometer, reflux condenser, and heating mantle was introduced 103 g (½ mole) 2,4-ditertiary butyl phenol, 0.3 g of 2-mercapto thiazoline and 100 cc of hexane. 23.0 g (1/6 mole) of phosphorus trichloride was then added and the mixture was heated to reflux temperature for eight hours. Nitrogen was passed through the hot solution to sweep out any residual hydrogen chloride. A stirrer was attached and the mix was stirred and cooled (finally to 10° C.) whereupon tris(2,4-ditertiary butyl phenyl) phosphite separated as a white crystalline solid. This was filtered off and washed with 50 cc of heptane. The dried product weighed 87.6 g (81% of theory). The material melted at 180°-184° C.

In a 500 ml 3-necked flask equipped with thermometer, reflux condenser, and heating mantle was introduced 103 g (½ mole) 2,4-ditertiary butyl phenol, 0.3 g of 2-mercapto benzoxazole and 100 cc of hexane. 23.0 g (1/6 mole) of phosphorus trichloride was then added and the mixture was heated to reflux temperature for eight hours. Nitrogen was passed through the hot solution to sweep out any residual hydrogen chloride. A stirrer was attached and the mix was stirred and cooled (finally to 10° C.) whereupon tris(2,4-ditertiary butyl phenyl) phosphite separated as a white crystalline solid. This was filtered off and washed with 50 cc of heptane. The dried product weighed 87.6 g (81% of theory). The material melted at 180°–182° C.

Example 9

Preparation of tris (2.4-di-tertiary amyl phenyl) phosphite (2-mercapto benzothiazole catalyst)

117 g (½ mole) of 2,4-di-tertiary amyl phenol, 0.3 g 2-mercapto benzothiazole and 100 cc of heptane were charged into a 500 ml 3-neck flask. 23.0 g (1/6 mole) of phosphorus trichloride was added. The mixture was heated to reflux for seven hours, after which time the evolution of hydrogen chloride virtually ceased. Nitrogen gas was passed through the solution to carry out any residual hydrogen chloride. The clear solution was placed in a vacuum evaporator and the heptane was removed. The oily residue weighed 129 g. This was treated with 200 cc methyl alcohol whereupon a white crystalline solid separated. This product was filtered off and washed with 50 cc of methyl alcohol and dried. The resulting tris (2,4-di-tertiary amyl phenyl) phosphite weighed 98.4 g(88%Theory) and melted sharply at 103° C. Carbon, hydrogen and nitrogen analyses gave the following:

|     | Calculated | Found |
| --- | --- | --- |
| % C | 78.9 | 79.09 |
| % H | 10.27 | 10.11 |
| % P | 4.2 | 4.24 |

EXAMPLES 10–22 RECYCLE OF SOLVENT AND CATALYST

Several series of experiments were conducted to illustrate the excellent results observed when the solvent filtrate from an initial preparation (containing the catalyst) is recharged into the reaction vessel along with new charges of hindered phenol and phosphorus trichloride.

Recycle Series (A) N-cyclohexyl benzothiazole-2 sulfenamide was used as Catalyst in Examples 10–13

Example 10

In a 500 ml 3-necked flask equipped with thermometer, reflux condenser, and heating mantle was introduced 103 g (½ mole) 2,4-ditertiary butyl phenol, 0.3 g of N-cyclohexyl benzothiazole-2-sulfenamide and 100 cc of hexane. 23.0 g (1/6 mole) of phosphorus trichloride was then added and the mixture was heated to reflux temperature for eight hours. Nitrogen was passed through the hot solution to sweep out any residual hydrogen chloride. A stirrer was attached and the mix was stirred and cooled (finally to 10° C.) whereupon tris(2,4-ditertiary butyl phenyl) phosphite separated as a white crystalline solid. This was filtered off and washed with 50 cc of heptane. The dried product weighed 80.4 g (74% of theory). The material melted at 178°–184° C.

Example 11

The combined filtrate and washings from 10 above (containing the catalyst) was recharged into the reaction flask, along with 103 g of 2,4-ditertiary butyl phenol and 23.0 g phosphorus trichloride. After heating to reflux for eight hours the solution was stirred and cooled and the filtered product was washed with 50 cc of heptane. The dried crystalline solid weighed 101.67 g and melted at 183°–184° C.

Example 12

The filtrate from 11 above was recharged into the reaction flask, along with 103 g 2,4-ditertiarybutyl phenol and 23 g phosphorus trichloride. After eight hours reflux, the mixture was cooled to 10° C., filtered and worked up by washing with 50 cc heptane. The product weighed 95.2 g. and melted at 183°–185° C.

Example 13

The filtrate from 12 above was heated with 103 g 2,4-ditertiary butyl phenol and 23 g phosphorus trichloride for eight hours at reflux. The solution, upon stirring and cooling deposited the crystalline product, after washing with 50 cc of heptane the product (when dry), weighed 96.68 g and melted at 182°–185° C.

Recycle Series (B) (N,N-Dicyclohexyl benzothiazole-2-sulfenamide as catalyst).

Example 14

Following the general procedure outlined in Series (A), above, 103 g of 2,4-ditertiary butyl phenol, 0.3 g N,N-dicyclohexyl benzothiazole-2-sulfenamide and 100 cc of heptane were treated with 23 g of phosphorus trichloride and heated to reflux for eight hours. The product, after washing with hexane and drying weighed 81.9 g and melted at 180°–186° C.

Example 15

The filtrate and washings from Example 14 above were heated eight hours to reflux with 103 g of 2,4-ditertiary butyl phenol and 23 g phosphorus trichloride. The filtered, washed (50 cc heptane) and dried product weighed 88.7 g and melted at 183°–185° C.

Example 16

The filtrate and washings from Example 15 above were again heated with 103 g 2,4-ditertiary butyl phenol and 23 g phosphorus trichloride. The product in this case weighed 83.09 g and melted at 183°–185° C.

Recycle Series (C) (Tetra methyl thiuram disulfide as catalyst).

Example 17

Employing the conditions described in the above experiments 103 g of 2,4-di-tertiary butyl phenol, 0.3 g of tetramethyl thiuram disulfide, 100 c of heptane and 23 g of phosphorus trichloride were reacted to form 78.29 g of product which melted at 179°–185° C.

Example 18

The filtrate and washings of Example 17 above were heated with a new charge of 103 g of 2,4-ditertiary butyl phenol and 23 g of phosphorus trichloride. The product weighed 91.63 g and melted at 182°–184° C.

Example 19

The filtrate and washings of 18 above were heated with 103 g ditertiary butyl phenol and 23.0 g phosphorus trichloride. Yield 89.3 g m.p. 180°-183° C.

Recycle Series (D) (Tetra methyl thiuram monosulfide as catalyst.

Example 20

In the manner described above 103 g of 2,4-ditertiary butyl phenol, 0.3 g tetra methyl thiuram mono sulfide, 100 cc heptane and 23 g phosphorus trichloride were reacted to yield 75.1 g of tris (2,4-ditertiary butyl phenyl) phosphite melting at 181°-186° C.

Example 21

The filtrate and washings of 20 above were refluxed for eight hours with 103 g of 2,4-ditertiary butyl phenol and 23.0 g phosphorus trichloride. The filtered and washed product weighed 96.4 g and melted at 181°-184° C.

Example 22

The filtrate and washings of 21 above were heated to reflux for eight hours with 103 g 2,4-ditertiary butyl phenol and 23 g phosphorus trichloride. Yield=88.9 g of product, m.p. 180°-183° C.

Examples 23-51

Additional preparations of tris(2,4-di-tertiary butyl phenyl)phosphite were carried out using varying amounts of 2-mercaptobenzothiazole as catalyst and following essentially the procedures set forth in Examples 1-9. The yields of these preparations along with reaction conditions and melting points of the product appear in Table I.

It can be seen from this Table that high yields of tris(2,4-di-tertiary butyl phenyl)phosphite can be obtained under certain reaction conditions using very low levels of catalyst.

EXAMPLES 52-63 AND COMPARATIVE EXPERIMENTS A, B, AND C

Again following the procedures outlined Examples 1-9, more tris(2,4-ditertiary butyl-phenyl)phosphite was prepared, using various catalysts within the scope of this invention, under differing reaction conditions. Also, Comparative Experiments A and B were run using prior art catalysts. Comparative Experiment C contained no catalyst.

Table II clearly shows that high yields can be obtained at very low catalyst levels and that these yields are superior to representative prior art catalysts.

Example 64

Tris(2,5-ditertiary butyl-4-hydroxy phenyl) phosphite.

The following were charged into a 500ml 3-neck flask: 111 g(½ mole) of 2,5-ditertiarybutyl hydroquinone, 0.3g mercaptobenzothiazole, 200 cc toluene, 23g phosphorus trichloride.

The mixture was gradually heated over a period of one hour to 81° C. whereupon hydrogen chloride was evolved. The mix was heated to near 120° C. for an additional seven hours. After standing overnight and cooling to room temperature the product crystallized. A stirrer was attached and the mixture was reheated to near 100° C. whereupon all had passed into solution. A stream of nitrogen gas was passed through the solution to remove residual traces of hydrogen chloride. The heater was removed and the mix was stirred and cooled to room temperature where upon the product crystallized.

The crystals were filtered and washed with 100 cc of toluene and then two 50 cc portions of hexane. The dried product weighed 102 g (88% of theory) and melted at 266°-273° C.

| Analysis: | Calculated | Found |
|---|---|---|
| % C | 72.62 | 72.53 |
| % H | 9.08 | 9.17 |
| % P | 4.47 | 4.66 |

Example 65

Tris(2-tertiary butyl-4-nonyl phenyl) phosphite

Using the same equipment described in Example 64, the following ingredients were charged into the 500 ml 3-neck flask:

1.38 g (½ mole) of 2-tertiary butyl-4-nonyl phenol
0.4 g mercaptobenzothiazole
23.0 g (1/6 mole) of phosphorus trichloride The mixture was gradually heated to 49° C. whereupon the mixture foamed quite badly. At this point 100 cc of heptane was added. Heating was continued and the temperature slowly increased to 96° C. over a two hour period. Hydrogen chloride was controllably evolved and no problem with foaming was encountered. The mixture was heated between 96° and 110° C. for a further ten hours. Nitrogen gas was passed through the hot reaction mixture to remove residual hydrogen chloride. The heptane was removed by heating the mixture under diminished pressure. The resulting product was a light colored viscous liquid. The yield was 140 grams (98.67% of theory).

Example 67

Reaction of phosphorus trichloride (1/3 mole) with 2,4-di-tertiary amyl phenol (2/3 mole) then with 2,4-ditertiary butyl phenol (1/3 mole).

One-third of a mole of phosphorus trichloride (46 g) was charged into a 500 ml 3-neck flask. One hundred cubic centimeters of toluene and 0.2 g mercaptobenzothiazole were added. Then 156 g (2/3 mole) of melted 2,4-di-tertiary amyl phenol was dropped in over a period of two hours, the temperature being maintained between 55° and 65° C.. The temperature was then increased to 120°-123° C. for two hours. Nitrogen gas was passed through the hot mix to remove residual hydrogen chloride. The mix stood over the weekend at room temperature. An infrared analysis showed no hydroxyl. The mixture was warmed to 60° C. and 68.3g (1/3 mole) of solid 2,4-di-tertiary butyl phenol was added. The mix was gradually heated to 127° C. (over two hours) and then heated near that temperature for three hours longer. Nitrogen gas was bubbled through the hot mix to remove residual hydrogen chloride. The toluene was removed by heating under diminished pressure. The residual product was a clear liquid that hardened to a clear glassy product on cooling. Three hundred cc of methanol was added and the mixture was stirred and heated to 60° C. The product gradually crystallized to a white powder. After standing in the methanol at room temperature overnight the solid product was filtered off and washed with 100 cc of methanol. The dried produce weighed 197.6 g (90% of theory). The material melted at 89°-93° C..

Example 68

Tris(2,4-ditertiary amyl phenyl) phosphite 117 g of 2,4-ditertiary amyl phenol ($\frac{1}{2}$ mole), 0.1 g mercaptobenzothiazole, 50 cc of xylene and 24 g (1/6 mole+5% excess) of phosphorus trichloride were charged into a 500 ml 3-neck flask equipped with a heating mantle, thermometer, reflux condenser and gas evolution tube. The mix was gradually heated to 72° whereupon hydrogen chloride was evolved. The mix was then heated gradually to 157° C. and kept near that temperature for a total heating time of eight hours. Nitrogen gas was passed through the hot mixture to remove residual hydrogen chloride. The xylene was removed by heating under diminished pressure. The solid product remaining in the flask was then treated with 100 cc methanol. The filtered product weighed 102.4 g. This melted at 97.5°-105.5° C. The product was then heated with 200 cc of hot methanol and filtered. The product weighed 101.5 g and melted at 105°-107.5° C.

TABLE I

PREPARATION of TRIS (2,4-di-tertiary butyl phenyl) PHOSPHITE

| Example No. | DTBP | Catalyst, g | Toluene, ml | PCl$_3$, g | Max. Temp., °C. | Time, Hours | Yield g | MP, °C. |
|---|---|---|---|---|---|---|---|---|
| 23 | 103 | 0.01 | 50 | 24 | 135 | 11 | 67.5 | 172.5–177.0 |
| 24 | 103 | 0.01 | 50 | 24 | 136 | 11 | 54.3 | 174.0–178.0 |
| 25 | 103 | 0.02 | 50 | 24 | 135 | 9 | 68.9 | 175.0–180.0 |
| 26 | 103 | 0.02 | 50 | 23 | 126 | 7 | 95.3 | 179.0–183.0 |
| 27 | 103 | 0.02 | 50 | 24 | 136 | 6 | 94.3 | 179.5–182.0 |
| 28 | 103 | 0.02 | 50 | 24 | 134 | 10 | 86.2 | 181.0–183.0 |
| 29 | 103 | 0.02 | 50 | 24 | 130 | 7 | 78.8 | 179.0–181.5 |
| 30 | 103 | 0.05 | 50 | 24 | 122 | 9 | 97.9 | 171.5–182.0 |
| 31 | 103 | 0.05 | 50 | 23 | 133 | 7 | 93.5 | 180.5–183.0 |
| 32 | 103 | 0.10 | 66 | 24 | 131 | 8.5 | 80.5 + 1.2 | 180.5–183.5 |
| 33 | 103 | 0.10 | 58 | 25 | — | 9 | 81.0 | 182.0–184.0 |
| 34 | 103 | 0.10 | 50 | 26 | 127 | 9 | 80.6 | 183.0–184.5 |
| 35 | 103 | 0.10 | 20* | 24 | 165 | 5 | 92.7 | 180.5–185.0 |
| 36 | 103 | 0.10 | 15* | 24 | 176 | 5 | 91.4 | 184.6–186.0 |
| 37 | 103 | 0.10 | 10* | 24 | 180 | 4.5 | 92.3 | 180.0–183.0 |
| 38 | 103 | 0.10 | 15* | 24 | — | 6 | 91.3 | 183.5–185.0 |
| 39 | 103 | 0.10 | 15* | 24 | — | 6 | 95.1 | 184.5–186.0 |
| 40 | 103 | 0.10 | 20* | 24 | 160 | 6 | 90.1 | 184.0–185.5 |
| 41 | 103 | 0.10 | 50 | 23 | 136 | 8 | 93.1 | 180.0–183.0 |
| 42 | 107 | 0.10 | 50 | 24 | 134 | 9 | 102.5 | 182.0–184.0 |
| 43 | 103 | 0.10 | 50 | 24 | 133 | 9 | 95.8 | 183.5–185.0 |
| 44 | 103 | 0.10 | 20* | 24 | 158 | 5 | 92.2 | 184.0–186.0 |
| 45 | 103 | 0.20 | 15 | 24 | 170 | 6 | 93.3 | 184.0–185.0 |
| 46 | 103 | 0.20 | 20* | 24 | 158 | 6 | 94.2 | 183.0–185.0 |
| 47 | 206 | 0.20 | 100 | 48 | 133 | 9 | 186.7 | 182.0–185.0 |
| 48 | 103 | 0.20 | 50 | 24 | 134 | 9 | 96.5 | 182.0–184.5 |
| 49 | 103 | 0.30 | 50 | 23 | 135 | 7 | 95.0 | 180.5–183.0 |
| 50 | 103 | 0.30 | 50 | 24 | 132 | 5 | 97.5 | 180.0–183.0 |
| 51 | 206 | 0.40 | 100 | 48 | 125 | 9 | 186.6 | 180.5–184.5 |

*Toluene not distilled off

TABLE II

PREPARATION of TRIS (2,4-di-tertiary butyl phenyl) PHOSPHITE

| Example No. | DTBP | Catalyst, g | Toluene, ml | PCl$_3$, g | Max. Temp., °C. | Time, Hours | Yield g | MP, °C. |
|---|---|---|---|---|---|---|---|---|
| 52 | 103 | 0.05$^1$ | 50 | 24 | 130 | 9 | 96.3 | 179.5–182.5 |
| 53 | 103 | 0.05$^2$ | 50 | 24 | 130 | 9 | 98.0 | 182.5–184.0 |
| 54 | 103 | 0.10$^3$ | 50 | 24 | 130 | 10 | 88.0 | 179.0–183.5 |
| 55 | 103 | 0.10$^4$ | 50 | 24 | 137 | 10 | 91.4 | 182.5–184.0 |
| 56 | 103 | 0.10$^5$ | 50 | 24 | 130 | 9 | 89.7 | 181.5–183.5 |
| 57 | 103 | 0.10$^6$ | 50 | 24 | 130 | 9 | 79.5 | 180.5–183.0 |
| 58 | 103 | 0.10$^3$ | 20$^{12}$ | 24 | 162 | 6 | 86.7 | 185.5–185.5 |
| 59 | 103 | 0.10$^9$ | 50 | 24 | 133 | 9 | 98.1 | 184.0–185.0 |
| 60 | 103 | 0.20$^6$ | 20$^{12}$ | 24 | 153 | 6 | 80.7 | 182.5–184.5 |
| 61 | 103 | 0.20$^7$ | 50 | 24 | 133 | 9 | 68.2 | 179.0–182.0 |
| 62 | 103 | 0.20$^8$ | 50 | 24 | 130 | 10 | 73.8 | 177.0–182.0 |
| 63 | 206 | 0.20$^9$ | 50 | 48 | 133 | 9 | 188.7 | 182.5–185.0 |
| Comparative Example | | | | | | | | |
| A | 103 | 0.10$^{10}$ | 50 | 24 | 129 | 9 | 45.5 + 1.6 | 173.0–178.0 |
| B | 103 | 0.10$^{11}$ | 50 | 24 | 130 | 9 | 52.8 | 175.5–180.0 |
| C | 103 | None | 50 | 23 | 136 | 8 | 0 | — |

COMPARATIVE EXAMPLE D

Example 68 except no catalyst added.

Yield - 9.16 g, mp 102.5°-107.5° C.

Various changes and modifications to the examples and description can be made by one skilled in the art without departing from the invention as hereinafter claimed.

I claim:

1. A process of making of triarylphosphite of formula (1)

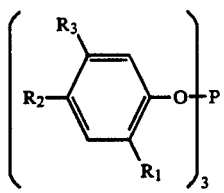

where $R_1$ is a $C_4$-$C_{18}$ tertiary alkyl, $R_2$ and $R_3$ are independently selected from hydrogen, hydroxy, $C_1$–$C_{20}$ straight chain or branched alkyl, $C_2$-$C_{20}$ cycloalkyl, $C_6$-$C_{20}$ aryl and $C_7$-$C_{20}$ aralkyl groups, said process comprising:

a) reacting a phosphorus trihalide with a hydroxy-substituted aromatic compound of the formula (2) in the presence or absence of a solvent, and in the presence of 0.005 to 10 mol %, relative to the hydroxy-substituted aromatic compound, of a catalyst to form a reaction mixture,

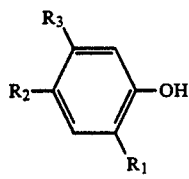

(b) isolating said triaryl phosphite from said reaction mixture; said catalyst being selected from the group consisting of a mercaptothiazole having the structure of formula (A), a dithiocarbamate of formula (B), mercaptothiazoline, mercaptobenzimidazole, and mercaptobenzoxazole,

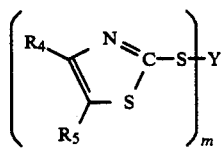

wherein $R_4$ and $R_5$ individually are hydrogen or $C_1$–$C_{12}$ alkyl; $R_4$ and $R_5$ combinedly may be benzo, $C_2$-$C_{18}$ branched or linear alkylene; when m is 1, Y is hydrogen, $C_2$-$C_8$ alkylamino, $C_3$-$C_8$ cycloalkylamino, a monovalent metal, morpholino, $C_1$-$C_8$alkyl, phenyl, or benzyl; and when m is 2, Y is a bond, divalent metal, $C_2$-$C_8$ alkylene, or $C_2$-$C_8$ alkylene diamine;

and wherein said dithiocarbamate has the structure of formula (B)

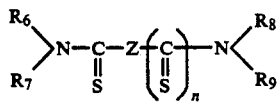

wherein n is 0 or 1 and Z is —S—, —S—S—, S—Metal—S—; when n is 1, then $R_6R_7$, $R_8$, $R_9$ are independently selected from hydrogen, $C_1$-$C_8$ branched or linear alkyl or phenyl; when n is 0, then $R_6$, $R_7$, $R_8$, $R_9$ are independently selected from $C_1$-$C_8$ alkyl, $C_1$-$C_8$ alkoxy, and $R_6$ and $R_7$ or $R_8$ and $R_9$ combinedly are $C_1$-$C_8$ oxydialkylene, benzo or $C_2$-$C_8$ alkylene.

2. A process according to claim 1 wherein the reacting step (a) is conducted in the presence of a solvent and the step (b) isolating step is conducted so as to leave a filtrate containing said solvent and substantially all of said catalyst.

3. A process according to claim 2 further comprising the repeating steps (a) and (b) sequentially for a plurality of iterations using said filtrate to replace substantially all of said solvent and said catalyst in the reacting step (a).

4. A process according to claim 1 wherein said isolating step (b) consists of crystallizing said triaryl phosphite.

5. A process according to claim 2 wherein said isolating step (b) consists of crystallizing said triaryl phosphite.

6. A process according to claim 2 wherein said solvent is used in step (a) and is selected from the group consisting of saturated or unsaturated aliphatics, aromatic and alkyl substituted aromatics, and halogenated aliphatics.

7. A process according to claim 6 wherein said solvent is selected from the group consisting of hexane, heptane, octane, nonane, decene, benzene, naptha, toluene, xylene, and mixtures thereof.

8. A process according to claim 5 wherein said crystallizing step includes the addition of an alcohol to said reaction mixture.

9. A process according to claim 1 wherein said catalyst is a mercaptothiazole having the structure of formula (A)

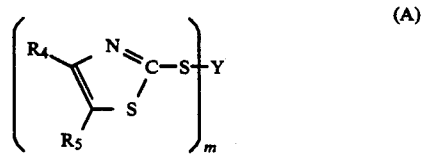

wherein $R_4$ and $R_5$ individually are hydrogen, $C_1$-$C_{12}$ alkyl; $R_4$ and $R_5$ combinedly may be benzo, $C_2$-$C_{18}$ branched or linear alkylene; when m is 1 , Y is hydrogen, $C_2$-$C_8$ alkylamino, $C_3$-$C_8$ cycloalkylamino, dicyclohexylamino, a monovalent metal, morpholine, $C_1$-$C_8$ alkyl, phenyl, or benzyl; and when m is 2, Y is a bond, divalent metal, $C_2$-$C_8$ alkylene, or $C_2$-$C_8$ alkylene diamine.

10. A process according to claim 1 wherein said catalyst is a dithiocarbamate having the structure of formula (B)

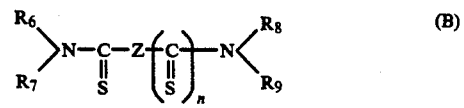

wherein n is 0 or 1 and Z is —S—, —S—S—, S—Metal—S—; when n is 1, then $R_6$, $R_7$, $R_8$, $R_9$ are independently selected from hydrogen, $C_1$-$C_8$ branched or linear alkyl, benzo or phenyl; when n is 0, then $R_6$, $R_7$, $R_8$, $R_9$ are independently selected from $C_1$-$C_8$ alkyl, $C_1$-$C_8$ alkoxy, and $R_6$ and $R_7$ or $R_8$ and $R_9$ combinedly are $C_2$-$C_8$ oxydialkylene.

11. A process according to claim 9 wherein $R_4$ and $R_5$ together with the two adjacent carbon atoms in the ring combinedly are benzo.

12. A process according to claim 11 wherein when m=2, Y is a bond or zinc and when m=1, Y is hydrogen, cyclohexylamino, dicyclohexyl amino, morpholino, alkylamino, 13. A process according to claim 11 wherein m is 1 and Y is hydrogen or cyclohexylamino.

14. A process according to claim 1 wherein said catalyst is selected from the group consisting of 2-mercaptobenzothiazole, zinc salt of 2-mercaptobenzothiazole, bis(benzothiazyl)disulfide, N-tertiary butyl benzothiazole-2-sulfenamide, N-cyclohexylbenzothiazole-2-sulfenamide, N,N-dicyclohexylbenzothiazole-2 -sulfenamide, N-2-morpholyl-benzothiazole-2-sulfenamide, 2-mercaptothiazole, 2-mercaptobenzoxazole and 2-mercaptothiazoline.

15. A process according to claim 1 wherein said catalyst is selected from the group consisting of tetra methylthiuram disulfide, tetraethylthiuram disulfide, tetrapropylthiuram disulfide, tetrabutylthiruam disulfide, tetrabenzyl thiuram disulfide, tetramethyl thiuram monosulfide, tetraethylthiuram monosulfide, tetrapropylthiuram monosulfide, tetrabutylthiuram monosulfide, and tetrabenzylthiuram monosulfide.

16. A process according to claim 1 wherein the hydroxy-substituted aromatic compound is selected from the group consisting of 2-t-butylphenol, 2,4-di-t-butylphenol, 2-(1,1-dimethylpropyl) phenol, 2,4-di-t-amylphenol, 2-t-octylphenol, 2,4 di-t-octylphenol, 2-t-nonylphenol, 2-t-dodecyl- phenol, 2-(dimethylbenzyl)phenol, 2,5-di-tert-butyl hydroquinone, 2,5-di-tert-amylhydroquinone.

17. A process according to claim 1 wherein no solvent is used in said reacting step (a) and said isolating step (b) includes addition of an alcohol to said reaction mixture.

18. A process comprising:
a) reacting a mole of phosphorus trihalide with bout two moles of a first hydroxy-substituted aromatic compound of the formula (2) and about one mole of a second hydroxy-substituted aromatic compound of formula (2) different from said first hydroxy-substituted aromatic compound, in the presence or absence of a solvent, and in the presence of 0.005 to 10 mol %, relative to the hydroxy-substituted aromatic compound, of a catalyst to form a reaction mixture,

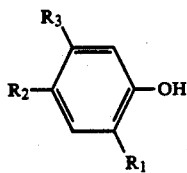

(2)

wherein $R_1$ is a $C_4$–$C_{18}$ tertiary alkyl, $R_2$ and $R_3$ are independently selected from hydrogen, hydroxy, $C_1$–$C_{20}$ independently selected from hydrogen, hydroxy, $C_1$–$C_{20}$ straight chain or branched alkyl, $C_3$–$C_{20}$ cycloalkyl, $C_6$–$C_{20}$ aryl and $C_7$–$C_{20}$ aralkyl groups;

b) isolating a triaryl phosphite from said reaction mixture, said catalyst being selected from the group consisting of tetra methylthiuram disulfide, tetraethylthiuram disulfide, tetrapropylthiuram disulfide, tetrabutylthiruam disulfide, tetrabenzyl thiuram disulfide, tetramethyl thiuram monosulfide, tetraethylthiuram monosufide, tetrapropylthiuram monosulfide, tetrabutylthiuram monosulfide, and tetrabenzylthiuram monosulfide.

19. A process for making tris (2,4-ditertiary butyl phenyl) phosphite comprising:
a) mixing a substantially stoichiometric amount of 2,4-ditertiary butylphenol with a phosphorus trihalide in a solvent in the presence of 0.005 to 10 mol percent relative to said 2,4 ditertiary butylphenol of a catalyst selected from the group consisting of 2-mercaptobenzothiazole, N-oxydiethylene benzothiazole 2-sulfenamide, tetra alkylthiuram disulfide, tetra alkylthiuram monosulfide, N-oxydiethylene thiocarbamyl-N-oxydiethylene sulfenamide, zinc salt of 2-mercaptobenzothiazole, zinc dialkyl dithiocarbamate, zinc dibenzyl dithiocarbamate, N-cyclohexyl-2-benzothiazole sulfenamide, and dicyclohexyl benzothiazole sulfenamide wherein alky is C1–C8 straight chain or branched alkyl;
b) heating to reflux temperature until hydrogen chloride generation has substantially ceased;
c) distilling off said solvent to leave a reaction mixture;
d) adding an alcohol to said reaction mixture;
e) crystallizing said tris (2,4 ditertiary butylphenyl)-phosphite; and
f) filtering of said tris (2,4-ditertiary butylphenyl) phosphite leaving a filtrate containing said catalyst.

20. A process for making tris (2,6-ditertiary butyl phenyl) phosphite comprising:
a) mixing a substantially stoichiometric amount of 2,6-ditertiary butylphenol with a phosphorus trihalide in a solvent in the presence of 0.005 to 10 mol percent relative to said 2,4-ditertiary butylphenol of a catalyst selected from the group consisting of 2-mercaptobenzothiazole, N-oxydiethylene benzothiazole -2-sulfenamide, tetra alkylthiuram disulfide, tetra alkylthiuram monosulfide, N-oxydiethylene thiocarbamyl-N-oxydiethylene sulfenamide, zinc salt of 2-mercaptobenzothiazole, zinc dialkyl dithiocarbamate, zinc dibenzyl dithiocarbamate, N-cyclohexyl-2-benzothiazole sulfenamide; t-butyl benzothiazole sulfenamide, and dicyclohexyl benzothiazole sulfenamide wherein alkyl is C1–C8 straight chain or branched alkyl;
b) heating to reflux temperature until hydrogen chloride generation has substantially ceased;
c) distilling off said solvent to leave a reaction mixture;
d) adding an alcohol to said reaction mixture;
e) crystallizing said tris (2,6-ditertiary butylphenyl)-phosphite; and
f) filtering of said tris (2,6-ditertiary butylphenyl) phosphite leaving a filtrate containing said catalyst.

* * * * *

UNITED STATES PATENT AND TRADEMARK OFFICE
CERTIFICATE OF CORRECTION

PATENT NO. : 5,254,709

DATED : October 19, 1993

INVENTOR(S) : Byron A. Hunter

It is certified that error appears in the above-indentified patent and that said Letters Patent is hereby corrected as shown below:

On the title page: Item [75] first inventor is misspelled. Change from "Bryon" to "Byron".

Column 15, line 12, change "$C_1 14\ C_{20}$" to "$C_1-C_{20}$"

Signed and Sealed this

Third Day of May, 1994

Attest:

BRUCE LEHMAN

*Attesting Officer*     Commissioner of Patents and Trademarks